US006602521B1

United States Patent
Ting et al.

(10) Patent No.: US 6,602,521 B1
(45) Date of Patent: Aug. 5, 2003

(54) MULTIPLEX DRUG DELIVERY SYSTEM SUITABLE FOR ORAL ADMINISTRATION

(75) Inventors: Richard Ting, Danville, CA (US); Charles Hsiao, Livermore, CA (US)

(73) Assignee: Impax Pharmaceuticals, Inc., Hayward, CA (US)

( * ) Notice: Subject to any disclaimer, the term of this patent is extended or adjusted under 35 U.S.C. 154(b) by 0 days.

(21) Appl. No.: 09/164,642

(22) Filed: Sep. 29, 1998

(51) Int. Cl.[7] .............................. A61K 9/24; A61K 9/20; A61K 9/44
(52) U.S. Cl. .................. 424/471; 424/464; 424/467; 424/468; 424/471; 424/472; 424/475; 424/476
(58) Field of Search .................... 424/464, 472, 424/467, 468

(56) References Cited

U.S. PATENT DOCUMENTS

| | | | |
|---|---|---|---|
| 3,336,200 A | * | 8/1967 | Krause et al. |
| 4,834,984 A | * | 5/1989 | Goldie et al. |
| 4,894,240 A | | 1/1990 | Geoghegan et al. ......... 424/497 |
| 5,017,381 A | * | 5/1991 | Maruyama et al. ......... 424/472 |
| 5,320,853 A | | 6/1994 | Noda et al. ................. 424/472 |
| 5,439,689 A | | 8/1995 | Hendrickson et al. ...... 424/490 |
| 5,474,786 A | | 12/1995 | Kotwal et al. ............... 424/472 |

FOREIGN PATENT DOCUMENTS

| FR | 2585948 A1 | 2/1987 |
|---|---|---|
| FR | 2 585 948 | * 2/1987 |

OTHER PUBLICATIONS

Georgarakis et al., Development of a New Controlled Release Theophylline Tablet: In Vitro and In Vivo Studies, Drug Development of Industrial Pharmacy 16/2 pp 315–329, 1990.*
Physician's Desk Reference, 53rd Edition (1997), Calan® SR and Isoptin® SR.*
English translation of Turlier (French Patent No. 2 585 948 A1), Feb. 1987.*
{711} Dissolution; USP 23; Physical Tests {711} 1791–1793, 2185, 2577–2578, 2833–2834,3208–3209,3495,3794. (1995).
{724} Drug Release; USP 23; Physical Tests 1793–1799, 2534–2536, 2709–2715, 3012–3017, 3209–3215, 3468–3474. (1995).

* cited by examiner

*Primary Examiner*—Carlos A. Azpuru
*Assistant Examiner*—Micah-Paul Young
(74) *Attorney, Agent, or Firm*—Fleshner & Kim, LLP

(57) ABSTRACT

A multiplex drug delivery system suitable for oral administration containing at least two distinct drug dosage packages, which exhibit equivalent dissolution profiles for an active agent when compare to one another and when compared to that of the entire multiplex drug delivery unit, and substantially enveloped by a scored film coating that allows the separation of the multiplex drug delivery system into individual drug dosage packages can provide a convenient and cost effective drug delivery unit, particularly for patients with a regimen of prescribed dosages that varies during their treatment period.

14 Claims, 3 Drawing Sheets

(Cross section of X axis)

(Cross section of Y axis)

(Cross section of X axis)

(Cross section of Y axis)

MULTIPLEX DRUG DELIVERY SYSTEM SUITABLE FOR ORAL ADMINISTRATION

FIELD OF THE INVENTION

The present invention relates to a single drug delivery unit suitable for oral administration containing at least two distinct drug dosage packages. This multiplex system contains at least two immediate-release compartments substantially enveloped by a scored extended-release compartment. The scored nature of the extended-release *compartment facilitates the separation by the patient of the multiplex drug delivery system into individual drug dosage packages for oral administration of the prescribed dosage. Upon separation, each individual drug dosage package can exhibit an equivalent, and preferably identical, release profile for the active agent as compared to one another and to that of the entire multiplex system. Accordingly, in a preferred embodiment, the separability of the multiplex drug delivery system enables its use throughout the entire course of a varying dosage regimen, and thus, facilitates cost effective patient compliance.

BACKGROUND OF THE INVENTION

Drug efficacy depends upon the maintenance of the proper therapeutic levels of the drug over the required treatment period. With respect to orally administered drugs, the effectiveness of treatment depends, in part or sometimes in whole, on patient compliance with the prescribed dosage regimen. Particularly where the prescribed dosage increases or decreases during the treatment period, patient compliance can suffer because of the unavailability of, or inconvenience in obtaining, the appropriate dosage of the prescribed medication at different times.

It would therefore be beneficial for patients to have one drug delivery unit that allows patients themselves to regulate the amount of drug to administer. Such a capability would enable patients to use the same drug delivery unit throughout their entire treatment period even where their prescribed dosage changes during that time. Patients in such circumstances would have the convenience and cost effectiveness of obtaining in one unit and at the same time the different dosages of their prescribed drug that would be needed during their treatment period.

A valuable contribution to the art therefore would be the development of a multiplex drug delivery system suitable for oral administration containing at least two immediate-release compartments substantially enveloped by a scored extended-release compartment that facilitates the separation of the multiplex drug delivery system into individual drug dosage packages for oral administration of the prescribed dosage, each of which can exhibit an equivalent, and preferably identical, release profile for the active agent as compared to one another and to that of the entire multiplex system.

SUMMARY OF THE INVENTION

Accordingly, an objective of the present invention is a single drug delivery unit suitable for oral administration that patients could separate into individual drug dosage packages. These individual drug dosage packages can exhibit an equivalent, and preferably identical, release profile for the active agent when compared to one another or when compared to the entire, intact multiplex drug delivery system.

The present invention accomplishes this objective through a multiplex drug delivery system suitable for oral administration containing at least two immediate-release compartments. The scored extended-release compartment of the invention allows the separation of the multiplex drug delivery system into individual drug dosage packages for oral administration of the prescribed dosage, each of which can exhibit an equivalent, and preferably identical, release profile for the active agent as compared to one another and to that of the entire multiplex system.

One preferred embodiment of the claimed invention is a multiplex drug delivery system suitable for oral administration comprising at least two immediate-release compartments substantially enveloped by a scored extended-release compartment. The extended-release compartment can comprise a combination of a hydrophobic and a hydrophobic material. In such an embodiment, the hydrophilic polymer(s) dissolves away to weaken the extended-release compartment, while the hydrophobic material retards the water, thus helping to preserve the integrity of the drug delivery system. Where the immediate-release compartments are inert (i.e., do not comprise an active agent), they can facilitate a bursting effect, which can disrupt any remaining integrity of the extended-release compartment.

In another preferred embodiment of the claimed invention, each immediate-release compartment further comprises an effective amount of an active agent, or a pharmaceutically acceptable salt thereof and the scored extended-release compartment further comprises an effective amount of an active agent, or a pharmaceutically acceptable salt thereof, in a compressed blend with the combination of a hydrophilic polymer and a hydrophobic material.

In a further preferred embodiment, each immediate-release compartment further comprises an effective amount of an active agent, or a pharmaceutically acceptable salt thereof, in a compressed blend with a polymer. In one other preferred embodiment, the scored extended-release compartment further comprises an effective amount of an active agent, or a pharmaceutically acceptable salt thereof, in a compressed blend with the combination of a hydrophilic polymer and a hydrophobic material. By varying the composition of the polymer(s) in the immediate-release compartments and/or the relative composition of the hydrophilic polymer and hydrophobic material in the extended-release compartment, the respective time periods for the dissolution of the active agent or the bursting effect can be adjusted.

In a preferred embodiment of the claimed invention, the active agent contained in the multiplex drug delivery system can be a drug. In other embodiments, that drug can be a therapeutic or a prophylactic drug.

In one preferred embodiment of the claimed invention, the drug of the multiplex drug delivery system can be diltiazem, trapidil, urapidil, benziodarone, dipyridamole, isosorbide mononitrate, or lidoflazine. In another embodiment, the drug can be a non-steroidal antiinflammatory drug (NSAID) or steroidal antiinflammatory drug. In an embodiment, the steroidal antiinflammatory drug can be diclofenac sodium, ibuprofen, ketoprofen, diflunisal, piroxicam, motrin, or naproxen. In yet another embodiment, the drug can be acetaminophen, aldosterone, alprenolol, amitryptyline, aspirin, beclomethasone, diproprionate, bromocriptine, butorphanol tartrate, chlormethiazole, chlorpheniramine, chlorpromazine HCl, cimetidine, codeine, cortisone, cyclobenzamine HCl, desmethylimipramine, dextropropoxyphene, dihydroergotamine, diltiazem HCl, dobutamine HCl, domperidone, dopamine HCl, doxepin HCl, epinephrine, ergoloid mesylates, ergotamine tartrate estradiol, ethinylestradiol, flunisolide, fluorouracil, flurazepam HCl, 5-fluoro-21-deoxyuridine, furosemide, glipizide, glyburide, glyceryl trinitrate, guanethidine sulfate, hydralazine HCl, imipramine HCl, indoramin, isoethorine HCl, isoethrine mesylate, isoprenaline, isoproterenol sulfate, isosorbide dinitrate, levallorphan tartrate, levodopa, lidocaine HCl, lignocaine, lorcainide, meperidine HCl, 6-mercaptopurine, metaproterenol sulfate, methoxamine HCl, methylphenidate, methylpreonisolone, methyltestosterone mesylate, metoclopramide, metoprolol tartrate, morphine sulfate, nalbuphine HCl, naloxone HCl, neostigmine, nifedipine, nitrendipine, nitroglycerin, norepinephrine bitartrate, norethindrone, nortriptylene HCl, oxprenolol, oxyphenbutazone, penicillamine, pentazocine HCl, pentazocine lactate, pentobarbital, petnidine, phenacetin, phentolamine HCl, phentolamine mesylate, phenylephrine HCl, phenylephrine bitartrate, phenytoin, pindolal, prazosin, prednisone, progesterone, propoxyphene HCl, propoxyphene napsylate, propranolol HCl, quinidine, reserpine, ritodrine HCl, salicylamide, salbutamol, secobarbital, testosterone, terbutaline, timolol maleate, tolbutamide, or verapamil HCl.

In one other preferred embodiment of the claimed invention, the active agent can preferably be isosorbide-5-mononitrate.

In a preferred embodiment, the active agent of the multiplex drug delivery system can exhibit the following in vitro dissolution profile when measured in a type 2 dissolution apparatus (paddle) according to U.S. Pharmacopeia XXII at 37° C±0.5° C. in deionized water at 75 rotations per minute:

from about 0% to about 90% of said active agent is released between 1 hour and 16 hours of measurement in said apparatus; and from about 0% to about 100% of said active agent is released between 1.5 hours and 28 hours after measurement in said apparatus.

In such a preferred embodiment, the active agent of the multiplex drug delivery system can be isosorbide-5-mononitrate.

In still another preferred embodiment, the active agent of the multiplex drug delivery system can exhibit the following in vitro dissolution profile when measured in a type 2 dissolution apparatus (paddle) according to U.S. Pharmacopeia XXII at 37° C.±0.5° C. in deionized water at 75 rotations per minute:

from about 10% to about 75% of said active agent is released between 1 hour and 5 hours of measurement in said apparatus; and no less than about 90% of said active agent is released after 6 hours of measurement in said apparatus.

In one preferred embodiment of the claimed invention, the polymer of the multiplex drug delivery system can be alginic acid, carboxymethylcellulose calcium, carboxymethylcellulose sodium, colloidal silicon dioxide, guar gum, magnesium aluminum silicate, methylcellulose, microcrystalline cellulose, cellulose, pregelatinized starch, sodium alginate, starch, ethylcellulose, gelatin, hydroxyethyl cellulose, hydroxypropyl cellulose, hydroxypropyl methylcellulose, polymethacrylates, povidone, shellac, or zein, and preferably hydroxypropyl methylcellulose.

In yet another preferred embodiment, the hydrophilic polymer of the multiplex drug delivery system can be carboxymethylcellulose, guar gum, hydroxyethyl cellulose, hydroxypropyl cellulose, hydroxypropyl methylcellulose, methylcellulose, or povidone, and preferably hydroxypropyl methylcellulose.

In a preferred embodiment of the claimed invention, the hydrophobic material of the multiplex drug delivery system can be carnauba wax, ethylcellulose, glyceryl palmitostearate, hydrogenated castor oil, hydrogenated vegetable oil, microcrystalline wax, polymethacrylates, or stearic acid, and preferably hydrogenated vegetable oil.

The present invention also accomplishes these and other objectives through a method for preparing a multiplex drug delivery system suitable for oral administration comprising the steps of combining an effective amount of an active agent, or a pharmaceutically acceptable salt thereof, and a polymer to form at least two immediate-release compartments; combining an effective amount of an active agent, or a pharmaceutically acceptable salt thereof, and a hydrophilic polymer and a hydrophobic material to form an extended-release compartment; press coating the extended-release compartment to substantially envelop the at least two immediate-release compartments, and scoring the extended-release compartment such that the immediate-release compartments are separable.

In a preferred embodiment, the method for preparing a multiplex drug delivery system suitable for oral administration can include combining by blending, perforated pan coating, fluidized particle coating, wet granulation, fluid-bed granulation, or dry granulation according to methods recognized in the art.

Other objects, features and advantages of the present invention will become apparent from the following detailed description. The detailed description and the specific examples, however, indicate only preferred embodiments of the invention. Various changes and modifications within the spirit and scope of the invention will become apparent to those skilled in the art from this detailed description.

In this preferred embodiment, the multiplex system consists of an oblong tablet scored in the middle to allow for easy breaking of the tablet. Each half of the tablet contains an immediate-release compartment located concentrically within the round tablet edges, allowing for a slightly thicker wall from the center edge when the tablet is broken in half. The distance between immediate-release compartments need not be greater than twice the distance between the interface of the immediate-release and extended-release compartments and that of the extended-release compartment and the outer surface or optional cosmetic compartment, so long as once separated, each individual drug dosage package can exhibit an equivalent, and preferably identical, release profile for the active agent as compared to one another and to that of the entire multiplex system.

Figure 1:
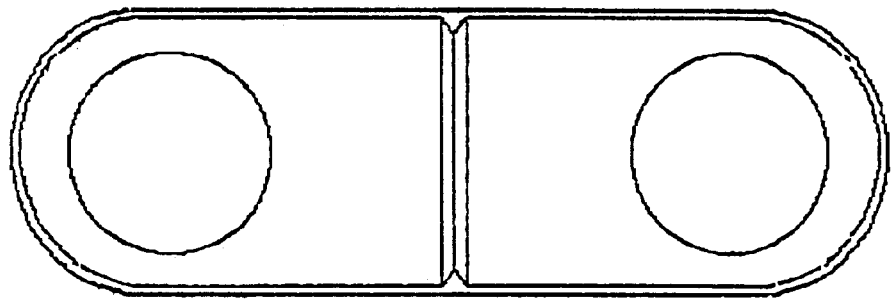
FIG. 1 is a schematic of one preferred embodiment of the multiplex drug delivery system suitable for oral administration, which contains two immediate-release compartments substantially enveloped by a scored extended-release compartment. The scored extended-release compartment of the invention allows the separation of the multiplex drug delivery system into individual drug dosage packages for oral administration of the prescribed dosage, each of which can exhibit an equivalent, and preferably identical, release profile for the active agent as compared to one another and to that of the entire multiplex system.
Figure 1:
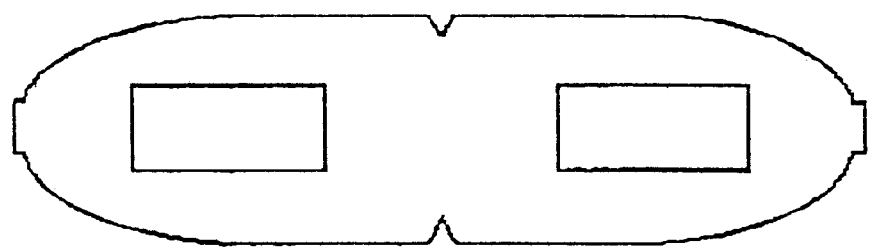
Figure 2:
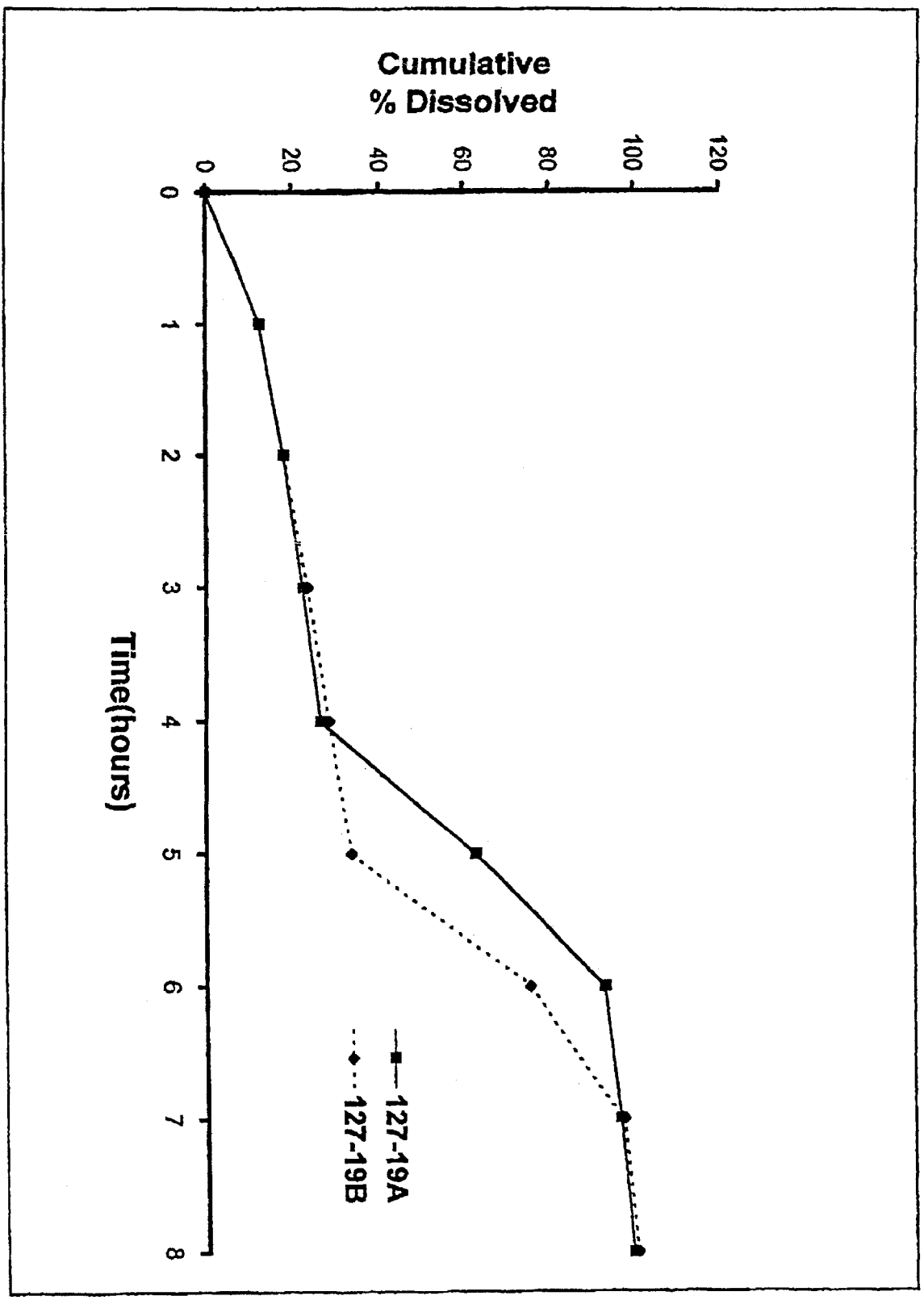

FIG. 2 is a graph showing the in vitro dissolution profile (% dissolved versus time) of isosorbide mononitrate extended release tablets (Lots 127-19A and 127-19B), according to an embodiment of the present invention, in deionized water using a type 2 dissolution apparatus (paddle method) at 37±0.5° C. at 75 rotations per minute (rpm). See U.S. Pharmacopeia XXII<711>Dissolution.

Figure 3:
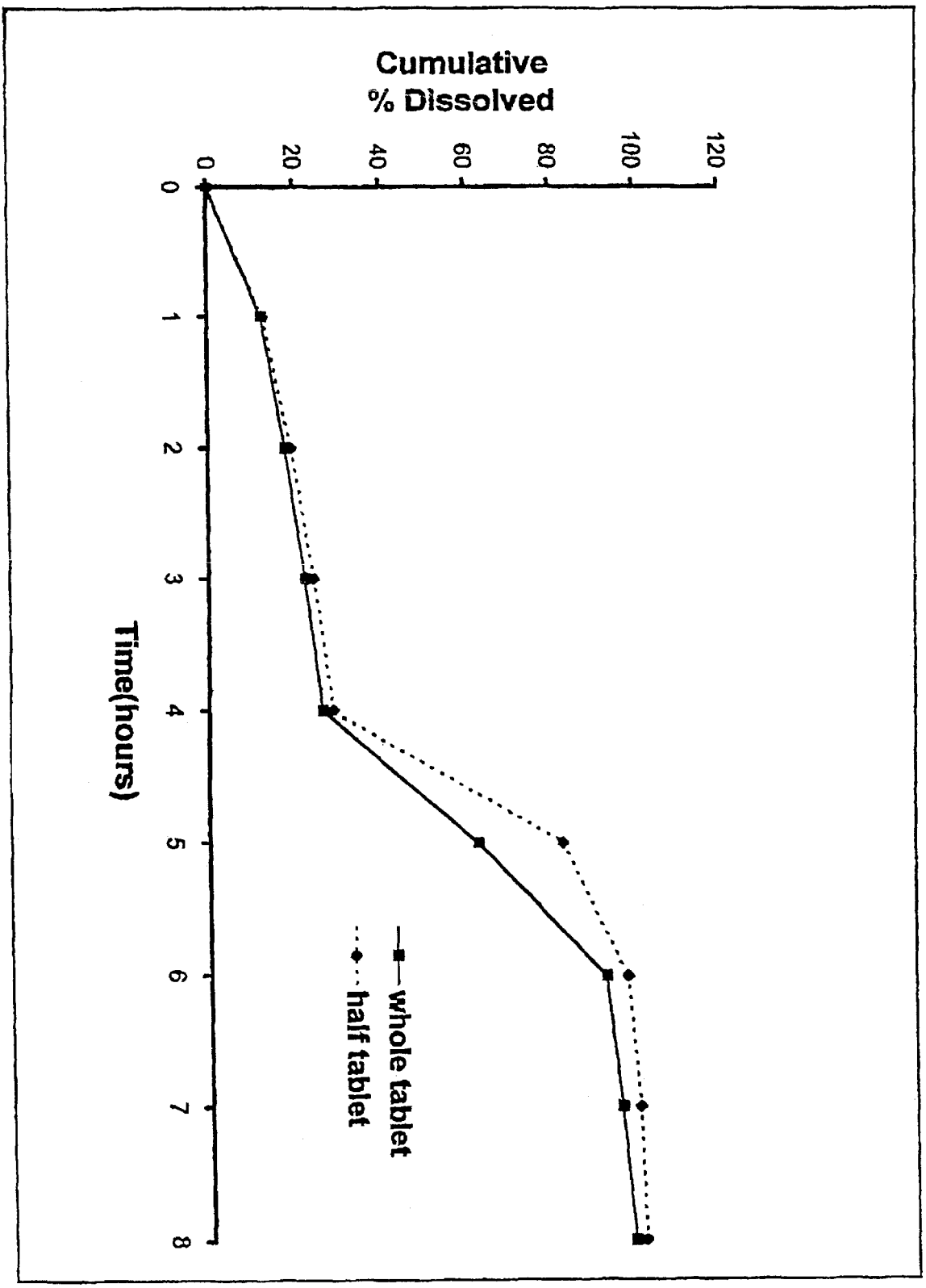

FIG. 3 is a graph showing the in vitro dissolution profiles (% dissolved versus time) of an entire multiplex drug delivery system containing two immediate-release compartments (each comprising the active agent isosorbide mononitrate) (Lot 127-19A "whole tablet"), and an individual drug dosage package thereof after separation (Lot 127-19A "half tablet"), according to respective embodiments of the present invention, in deionized water using a type 2 dissolution apparatus (paddle method) at 37±0.5° C. at 75 rotations per minute (rpm). See U.S. Pharmacopeia XXII <711>Dissolution.

DETAILED DESCRIPTION OF PREFERRED EMBODIMENTS

In accordance with the present invention, the term "active agent" includes one or more drugs, their pharmaceutically acceptable salts, pro-drug forms, metabolites, and derivatives.

Active agents include therapeutic or prophylactic compounds as described in the Physicians' Desk Reference, most preferably including (but not limited to) those prescribed for the prevention and/or treatment of angina and hypertension: diltiazem, trapidil, urapidil, benziodarone, dipyridamole, isosorbide mononitrate, and lidoflazine; and those prescribed for the prevention and/or treatment of rheumatic diseases such as rheumatoid arthritis: non-steroidal antiinflammatory drugs (NSAIDs) and steroidal antiinflanrmatory drugs such as diclofenac sodium, ibuprofen, ketoprofen, diflunisal, piroxicam, motrin, and naproxen, and combinations thereof.

The active agent of the present invention also preferably includes drugs that are subject to the first pass effect. Various examples of such drugs include (but are not limited to) acetaminophen, aldosterone, alprenolol, amitryptyline, aspirin, beclomethasone, diproprionate, bromocriptine, butorphanol tartrate, chlormethiazole, chlorpheniramine, chlorpromazine HCl, cimetidine, codeine, cortisone, cyclobenzamine HCl, desmethylimipramine, dextropropoxyphene, dihydroergotamine, diltiazem HCl, dobutamine HCl, domperidone, dopamine HCl, doxepin HCl, epinephrine, ergoloid mesylates, ergotamine tartrate estradiol, ethinylestradiol, flunisolide, fluorouracil, flurazepamn HCl, 5-fluoro-21-deoxyuridine, furosemide, glipizide, glyburide, glyceryl trinitrate, guanethidine sulfate, hydralazine HCl, imipramine HCl, indoramin, isoethorine HCl, isoethrine mesylate, isoprenaline, isoproterenol sulfate, isosorbide dinitrate, levallorphan tartrate, levodopa, lidocaine HCl, lignocaine, lorcainide, meperidine HCl, 6-mercaptopurine, metaproterenol sulfate, methoxamine HCl, methylphenidate, methylpreonisolone, methyltestosterone mesylate, metoclopramide, metoprolol tartrate, morphine sulfate, nalbuphine HCl, naloxone HCl, neostigmine, nifedipine, nitrendipine, nitroglycerin, norepinephrine bitartrate, norethindrone, nortriptylene HCl, oxprenolol, oxyphenbutazone, penicillamine, pentazocine HCl, pentazocine lactate, pentobarbital, petnidine, phenacetin, phentolamine HCl, phentolamine mesylate, phenylephrine HCl, phenylephrine bitartrate, phenytoin, pindolal, prazosin, prednisone, progesterone, propoxyphene HCl, propoxyphene napsylate, propranolol HCl, quinidine, reserpine, ritodrine HCl, salicylamide, salbutamol, secobarbital, testosterone, terbutaline, timolol maleate, tolbutamide, and verapamil HCl.

In a preferred embodiment of the present invention, the active agent may include the drug, isosorbide-5-mononitrate, an organic nitrate, which is a vasodilator with effects on both arteries and veins. The empirical formula is $C_6H_9NO_6$ and the molecular weight is 191.14. The chemical name for isosorbide mononitrate is 1,4:3,6-dihydro-D-glucitrol 5-nitrate.

Isosorbide mononitrate is the major active metabolite of isosorbide dinitrate and most of the clinical activity of the dinitrate can be attributable to the mononitrate. A principal pharmacological action of isosorbide mononitrate is relaxation of vascular smooth muscle and consequent dilatation of peripheral arteries and veins, especially the latter. Dilatation of the veins is known to promote peripheral pooling of blood and decrease venous return to the heart, thereby reducing left ventricular and diastolic pressure and pulmonary capillary wedge pressure (preload). Arteriolar relaxation reduces systemic vascular resistance, systolic arterial pressure, and mean arterial pressure (afterload). Dilation of the coronary arteries also occurs. The relative importance of preload reduction, afterload reduction, and coronary dilatation remains undefined. The mechanism by which isosorbide mononitrate relieves angina pecteria is not fully understood.

Isosorbide mononitrate is rapidly and completely absorbed from the gastrointestinal tract. In humans, isosorbide mononitrate is not subject to first pass metabolism in the liver. The overall elimination half-life of isosorbide mononitrate is about 6 hours. The rate of clearance is the same in healthy young adults, and in patients with various degrees of renal, hepatic, or cardiac dysfunction.

In accordance with the present invention, the term "polymer" includes single or multiple polymeric substances, which can swell, gel, degrade or erode on contact with anaqueous environment (e.g., water), such as one or more of alginic acid, carboxymethylcellulose calcium, carboxymethylcellulose sodium, colloidal silicon dioxide, guar gum, magnesium aluminum silicate, methylcellulose, microcrystalline cellulose, cellulose, pregelatinized starch, sodium alginate, starch, ethylcellulose, gelatin, hydroxyethyl cellulose, hydroxypropyl cellulose, hydroxypropyl methylcellulose, polymethacrylates, povidone, pregelatinized starch, shellac, and zein, and combinations thereof.

The "hydrophilic polymers" of the present invention include one or more of carboxymethylcellulose, guar gum, hydroxyethyl cellulose, hydroxypropyl cellulose, hydroxypropyl methylcellulose, methylcellulose, and povidone. The "hydrophobic materials" of the present invention include one or more of carriauba wax, ethylcellulose, glyceryl palmitostearate, hydrogenated castor oil, hydrogenated vegetable oil, microcrystalline wax, polymethacrylates, and stearic acid.

Without further elaboration, it is believed that one skilled in the art, using the preceding description, can practice the present invention to the fullest extent. The following examples are illustrative only, and not limiting of the remainder of the disclosure in any way whatsoever.

EXAMPLES

The method below was employed to obtain a multiplex drug delivery system, the composition of which is set forth in the tables immediately following in Table 1:

Immediate-Release Compartment. Isosorbide mononitrate was first mixed with silicon dioxide in a Patterson-Kelley V-blender together with microcrystalline cellulose, croscarmellulose sodium, and magnesium stearate for 15 minutes. The powder blend was then compressed using a Manesty Dry-cota with a 3/16" diameter, round, flat-face punch and die set. The hardness of the tablets were maintained at 4±2kp.

Immediate-Release Compartment Plus Extended-Release Compartment

Isosorbide mononitrate was mixed with silicon dioxide in a Patterson-Kelley V-blender together with hydroxypropyl methylcellulose 2208, microcrystalline cellulose, hydrogenated vegetable oil, and magnesium stearate for 15 minutes. The core tablets were press-coated using a Korsch Core Coater 5/16"×3/4" capsule shape punches. The hardness of the tablets were maintained at 12±4 kp.

In addition, the formulation of respective release compartments can occur by appropriate granulation methods. In wet granulation, solutions of the binding agent (polymer) are added with stirring to the mixed powders. The powder mass is wetted with the binding solution until the mass has the consistency of damp snow or brown sugar. The wet granulated material is forced through a sieving device. Moist material from the milling step is dried by.placing it in a temperature controlled container. After drying, the granulated material is reduced in particle size by passing through a sieving device. Lubricant is added, and the final blend is then compressed.

In fluid-bed granulation, particles of inert material and/or active agent are suspended in a vertical column with a rising air stream. While the particles are suspended, the common granulating materials in solution are sprayed into the column. There is a gradual particle buildup under a controlled set of conditions resulting in tablet granulation. Following drying and the addition of lubricant, the granulated material is ready for compression.

In dry-granulation, the active agent, diluent, and lubricant are blended and compressed into large tablets. The compressed large tablets are comminuted through the desirable mesh screen by sieving equipment. Some more lubricant is added to the granulated material and blended gently. The material is then compressed into tablets.

TABLE 1

| | QUANTITY/TABLET | |
|---|---|---|
| | Example #1 | Example #2 |
| Immediate-Release (IR) Compartment | Lot 127-13 | Lot 127-13 |
| Isosorbide-5-mononitrate 80% w/lactose | 25.0 mg | 25.0 mg |
| Croscarmellose sodium | 1.1 mg | 1.1 mg |
| Microcrystalline cellulose | 28.2 mg | 28.2 mg |
| Colloidal Silicon dioxide | 0.2 mg | 0.2 mg |
| Magnesium stearate | 0.5 mg | 0.5 mg |
| Total: | 55.0 mg | 55.0 mg |
| IR Compartment Plus Extended-Release (ER) Compartment | Lot 127-19A | Lot 127-19B |
| IR Compartment (two cores) | 110.0 mg | 110.0 mg |
| Isosorbide-5-mononitrate 80% w/lactose | 37.5 mg | 37.5 mg |
| Hydroxypropyl methylcellulose, type 2208 | 201.6 mg | 288.0 mg |
| Microcrystalline cellulose | 245.5 mg | 245.5 mg |
| Hydrogenated vegetable oil, type 1 | 223.2 mg | 136.8 mg |
| Colloidal silicon dioxide | 3.6 mg | 3.6 mg |
| Magnesium stearate | 7.2 mg | 7.2 mg |
| Blue dye | 1.4 mg | 1.4 mg |
| Total: | 830.0 mg | 830.0 mg |

The invention has been disclosed broadly and illustrated in reference to representative embodiments described above. Those skilled in the art will recognize that various modifications can be made to the present invention without departing from the spirit and scope thereof.

What is claimed is:

1. A multiplex active agent delivery system in the form of a tablet suitable for oral administration, comprising two, three or four immediate release compartments wherein each immediate release compartment contains an active agent selected from the group consisting of diltiazem, trapidil, urapidil, benziodarone, dipyrudamole, isosorbide mononitrate, lidoflazine, non-steroidal anti-inflammatory drugs (NSAIDs), steroidal anti-inflammatory drugs, acetaminophen, aldosterone, alprenolol, amitryptyline, aspirin, beclomethasone, diproprionate, bromocriptine, butorphanol tartrate, chlormethiazole, chlorpheniramine, chlorpromazine HCl, cimetidine, codeine, cortisone, cyclobenzamine HCl, desmethylimipramine, dextropoxyphene, dihydroergotamine, diltiazem HCl, dobutamine HCl, domperidone, dopamine HCl, doxepin HCl, epinephrine, ergoloid mesylates, ergotamine tartrate estradiol, ethinylestradiol, flunisolide, fluorouracil, flurazepam HCl, 5-fluoro-21deoxyuridine, furosemide, glipizide, glyburide, glyceryl trinitrate, guanethidine sulfate, hydralazine HCl, indoramin, isoethorine HCl, isoethrine mesylate, isoprenaline, isoproterenol sulfate, isosorbide dinitrate, levodopa, lidocaine HCl, lignocaine, lorcainide, meperidine HCl, 6-mercaptopurine, metaproterenol sulfate, methoxamine HCl, methylphenidate, methyepreonisolone, methyltestosterone mesylate, metoclopramide, metoprolol tartrate, morphine sulfate, nalbuphine HCl, naloxone HCl, neostigmine, nifedipine, nitrendipine, nitroglycerin, norepineohrine bitartate, norethindore, nortriptylen HCl, oxprenolol, oxyphenbutzone, penicillamine, pentazocine HCl, pentazcine lactate, pentobarbital, petnidine, phenacetin, phentolamine HCl, phentolamine mesylate, phenylephrine HCl, phenylephrine bitartrate, phenytoin, pindolal, prazosin, prednisone, progesterone, propoxyphene HCl, propoxyphene napsylate, propranolol HCl, quinidine, reserpine, ritodrine HCl, salicyamide, salbutamol, secobarbital, testosterone, terbutaline, timolol maleate, tolbutamide, and verapamil HCl, and an extended release polymer outer layer which substantially envelops the immediate release compartments, wherein the tablet is scored such that when the active agent delivery system is separated along the score into sections, each of the sections contains an immediate release compartment within an extended release polymer outer layer, and wherein the active agent delivery system is not an osmotic pump, and wherein the active agents exhibit the following in vitro dissolution profile when measured in a type 1 dissolution apparatus (paddle) according to U.S. Pharmacopoeia XXII at 37° C.±0.5° C. in deionized water at 75 rotations per minute:

(a) from about 10% to about 75% of said active agent is released between 1 hour and 5 hours of measurement in said apparatus; and, (b) no less than about 90% of said active agent is released after 6 hours of measurement said apparatus.

2. The multiplex active agent delivery system of claim 1, wherein each of the immediate-release compartments contains an effective amount of the active agent.

3. The multiplex active agent delivery system of claim 2, wherein each of the immediate-release compartments contains an effective amount of the active agent, in a compressed blend with a polymer.

4. The multiplex active agent delivery system of claim 1, wherein the extended release polymer outer layer comprises an effective amount of the active agent, in combination with a hydrophilic material and a hydrophobic material.

5. The multiplex active agent delivery system of claim 4, wherein the extended-release polymer outer layer comprises an effective amount of the active agent, in a compressed blend with a combination of a hydrophilic polymer and a hydrophobic material.

6. The multiplex active agent delivery system of claim 2, wherein the active agent is a drug.

7. The multiplex active agent delivery system of claim 4, wherein the active agent is a drug.

8. The multiplex active agent delivery system of claim 3, wherein the polymer is selected from the group consisting of alginic acid, carboxymethylcellulose calcium, carboxymethylcellulose sodium, colloidal silicon dioxide, guar gum, magnesium aluminum silicate, methylcellulose, microcrystalline cellulose, cellulose, pregelatinized starch, sodium alginate, starch, ethylcellulose, gelatin, hydroxyethyl cellulose, hydroxypropyl cellulose, hydroxypropylmethyl cellulose, polymethacrylate, povidone, shellac and zein.

9. The multiplex active agent delivery system of claim 5, wherein the hydrophilic polymer is selected from the group consisting of carboxymethylcellulose, guar gum, hydroxyethyl cellulose, hydroxypropyl cellulose, hydroxypropylmethyl cellulose, methylcellulose and povidone.

10. The multiplex active agent delivery system of claim 5, wherein the hydrophobic material is selected from the group consisting of carnauba wax, ethylcellulose, glyceryl palmitostearate, hydrogenated castor oil, hydrogenated vegetable oil, microcrystalline wax, polymethacrylate and stearic acid.

11. The multiplex active agent delivery system of claim 2, wherein each section of the separated active agent delivery system exhibits an equivalent release profile for the active agent when compared to one another.

12. The multiplex active agent delivery system of claim 4, wherein each section of the separated active agent delivery system exhibits an equivalent release profile for the active agent when compared to one another.

13. The multiplex active agent delivery system of claim 2, wherein each section of the separated active agent delivery system exhibits an equivalent release profile for the active agent when compared to one another and when compared to the active agent delivery system in its entirety.

14. The multiplex active agent delivery system of claim 4, wherein each section of the separated active agent delivery system exhibits an equivalent release profile for the active agent when compared to one another and when compared to the active agent delivery system in its entirety.

* * * * *

UNITED STATES PATENT AND TRADEMARK OFFICE
CERTIFICATE OF CORRECTION

PATENT NO.    : 6,602,521 B1
DATED         : August 5, 2003
INVENTOR(S)   : Ting et al.

It is certified that error appears in the above-identified patent and that said Letters Patent is hereby corrected as shown below:

Column 1,
Line 11, change "*compartment" to -- compartment --.

Column 2,
Line 14, change "hydrophobic" to -- hydrophilic --.

Column 6,
Line 3, change "1,4:3,6-dihydro-D" to -- 1,4:3,6-dianhydro-D --.
Line 45, change "carriauba" to -- carnauba --.

Column 8,
Line 21, change "isoethorine HCI, isoethorine" to -- isoetharine HCI, isoetharine --.
Line 25, change "methyepreonisolone," to -- methylprednisolone, --.
Line 47, change "type 1" to -- type 2 --.

Signed and Sealed this

Tenth Day of August, 2004

JON W. DUDAS
*Acting Director of the United States Patent and Trademark Office*